US012596854B2

(12) United States Patent
Ramprasad et al.

(10) Patent No.: US 12,596,854 B2
(45) Date of Patent: Apr. 7, 2026

(54) SYSTEMS AND METHODS FOR MATERIAL SIMULATION

(71) Applicant: Georgia Tech Research Corporation, Atlanta, GA (US)

(72) Inventors: Rampi Ramprasad, Atlanta, GA (US); Anand Chandrasekaran, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1126 days.

(21) Appl. No.: 17/284,596

(22) PCT Filed: Oct. 11, 2019

(86) PCT No.: PCT/US2019/055919
§ 371 (c)(1),
(2) Date: Apr. 12, 2021

(87) PCT Pub. No.: WO2020/117370
PCT Pub. Date: Jun. 11, 2020

(65) Prior Publication Data
US 2021/0264080 A1 Aug. 26, 2021

Related U.S. Application Data

(60) Provisional application No. 62/744,593, filed on Oct. 11, 2018.

(51) Int. Cl.
| | |
|---|---|
| *G16C 60/00* | (2019.01) |
| *G06F 30/25* | (2020.01) |
| *G06N 3/04* | (2023.01) |
| *G06N 3/063* | (2023.01) |
| *G06N 3/08* | (2023.01) |
| *G06F 111/10* | (2020.01) |

(52) U.S. Cl.
CPC .............. *G06F 30/25* (2020.01); *G06N 3/04* (2013.01); *G06N 3/063* (2013.01); *G06N 3/08* (2013.01); *G16C 60/00* (2019.02); *G06F 2111/10* (2020.01)

(58) Field of Classification Search
None
See application file for complete search history.

(56) References Cited

U.S. PATENT DOCUMENTS

| | | |
|---|---|---|
| 2016/0232440 A1 | 8/2016 | Gregor et al. |
| 2016/0333538 A1 | 11/2016 | Shubert et al. |

OTHER PUBLICATIONS

Botu, Venkatesh, et al. "Machine learning force fields: construction, validation, and outlook." The Journal of Physical Chemistry C 121.1 (2017): 511-522. (Year: 2017).*

Chandrasekaran, A., Kamal, D., Batra, R. et al. Solving the electronic structure problem with machine learning. npj Comput Mater 5, 22 (2019) (Year: 2019).*

Batra, Rohit, et al. "General atomic neighborhood fingerprint for machine learning-based methods." The Journal of Physical Chemistry C 123.25 (2019): 15859-15866. (Year: 2019).*

Stoliaroff, Adrien, Stéphane Jobic, and Camille Latouche. "PyDEF 2.0: an easy to use post-treatment software for publishable charts featuring a graphical user interface." Journal of Computational Chemistry 39.26 (2018): 2251-2261. (Year: 2018).*

Gopejenko, V., Gopejenko, A. (2018). Using Applications and Tools to Visualize ab initio Calculations Performed in VASP. In: De Paolis, L., Bourdot, P. (eds) Augmented Reality, Virtual Reality, and Computer Graphics. AVR 2018. Lecture Notes in Computer Science( ), vol. 10850. (Year: 2018).*

International Search Report and Written Opinion from Application No. PCT/US2019/055919 (11 pages).

Ramprasad, et al., "Machine Learning in Materials Informatics: Recent Applications and Prospects," Computational 2017 Materials vol. 3, Article No. 54; pp. 14, 18-19.

Tang, et al., "An Atomistic Fingerprint Algorithm for Learning Ab Initio Molecular Force Fields," Cornell University/Computer Science/ Computational Engineering, Finance, and Science Dec. 14, 2017, pp. 5, 12-13.

* cited by examiner

*Primary Examiner* — Kaitlyn L Minchella
*Assistant Examiner* — Jonathan Edward Hayes
(74) *Attorney, Agent, or Firm* — TROUTMAN PEPPER LOCKE LLP; Ryan A. Schneider; Celeste K. Walker

(57) ABSTRACT

A system for a material simulation is disclosed. The system may receive an input structure for the material and identify a reference grid point for the material. The system may determine a scalar, vector, and tensorial component for the material. Further, the system may render the vector component and the tensorial component rotationally invariant. Next, the system may generate a first structure fingerprint for the material based on the scalar, vector component, and tensorial component. The system may map the structure fingerprint to stored atomic configurations and based on corresponding stored atomic configuration(s), may determine an approximate total electronic charge density and a plurality of approximate energy levels for the reference grid point. Based on the plurality of approximate energy levels, the system may determine a predictive local density of states for the reference grid point. The system may also generate and display a visual simulation of the material.

18 Claims, 7 Drawing Sheets

200

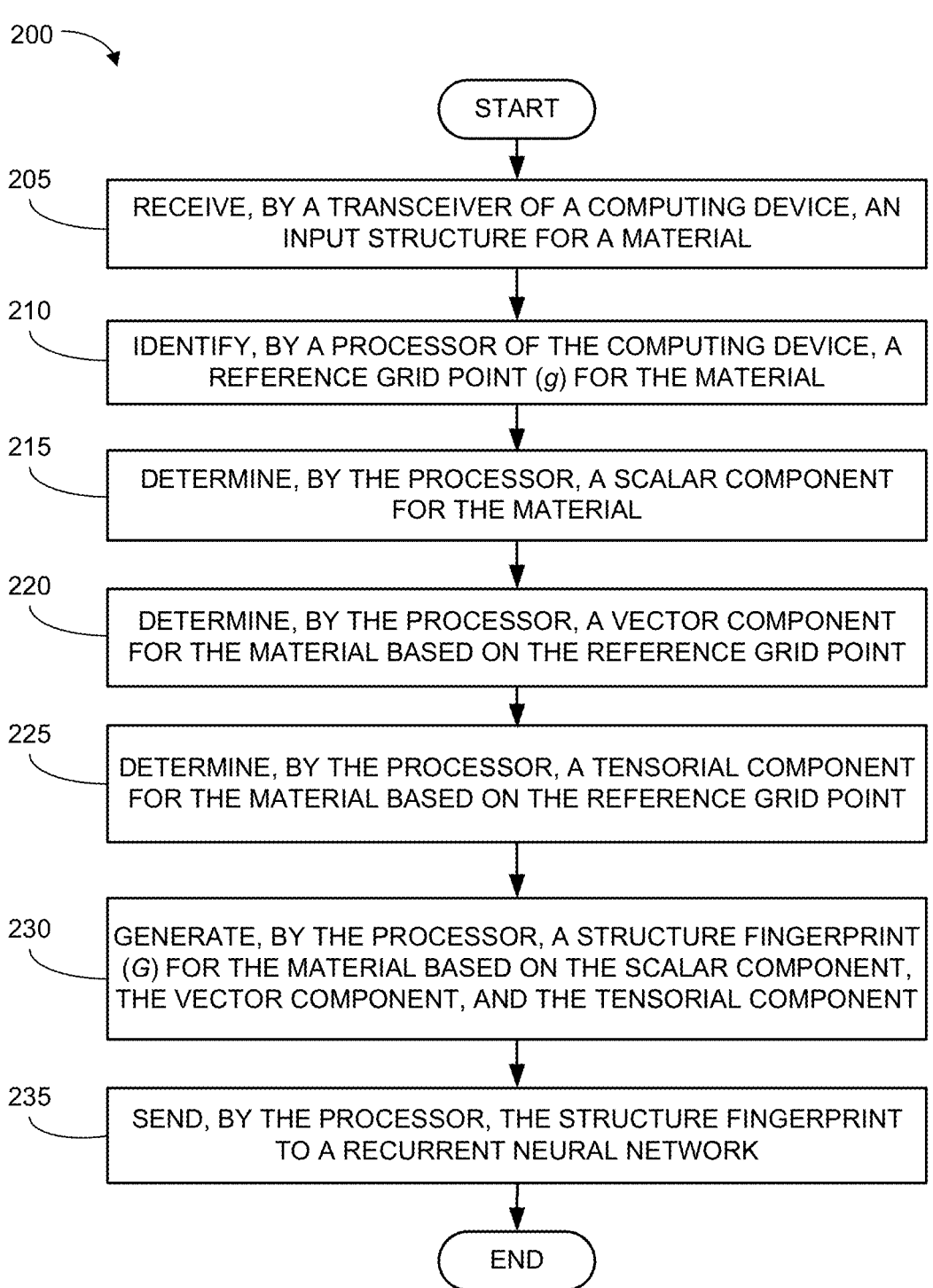

START

205 RECEIVE, BY A TRANSCEIVER OF A COMPUTING DEVICE, AN INPUT STRUCTURE FOR A MATERIAL

210 IDENTIFY, BY A PROCESSOR OF THE COMPUTING DEVICE, A REFERENCE GRID POINT ($g$) FOR THE MATERIAL

215 DETERMINE, BY THE PROCESSOR, A SCALAR COMPONENT FOR THE MATERIAL

220 DETERMINE, BY THE PROCESSOR, A VECTOR COMPONENT FOR THE MATERIAL BASED ON THE REFERENCE GRID POINT

225 DETERMINE, BY THE PROCESSOR, A TENSORIAL COMPONENT FOR THE MATERIAL BASED ON THE REFERENCE GRID POINT

230 GENERATE, BY THE PROCESSOR, A STRUCTURE FINGERPRINT ($G$) FOR THE MATERIAL BASED ON THE SCALAR COMPONENT, THE VECTOR COMPONENT, AND THE TENSORIAL COMPONENT

235 SEND, BY THE PROCESSOR, THE STRUCTURE FINGERPRINT TO A RECURRENT NEURAL NETWORK

END

*FIG. 2*

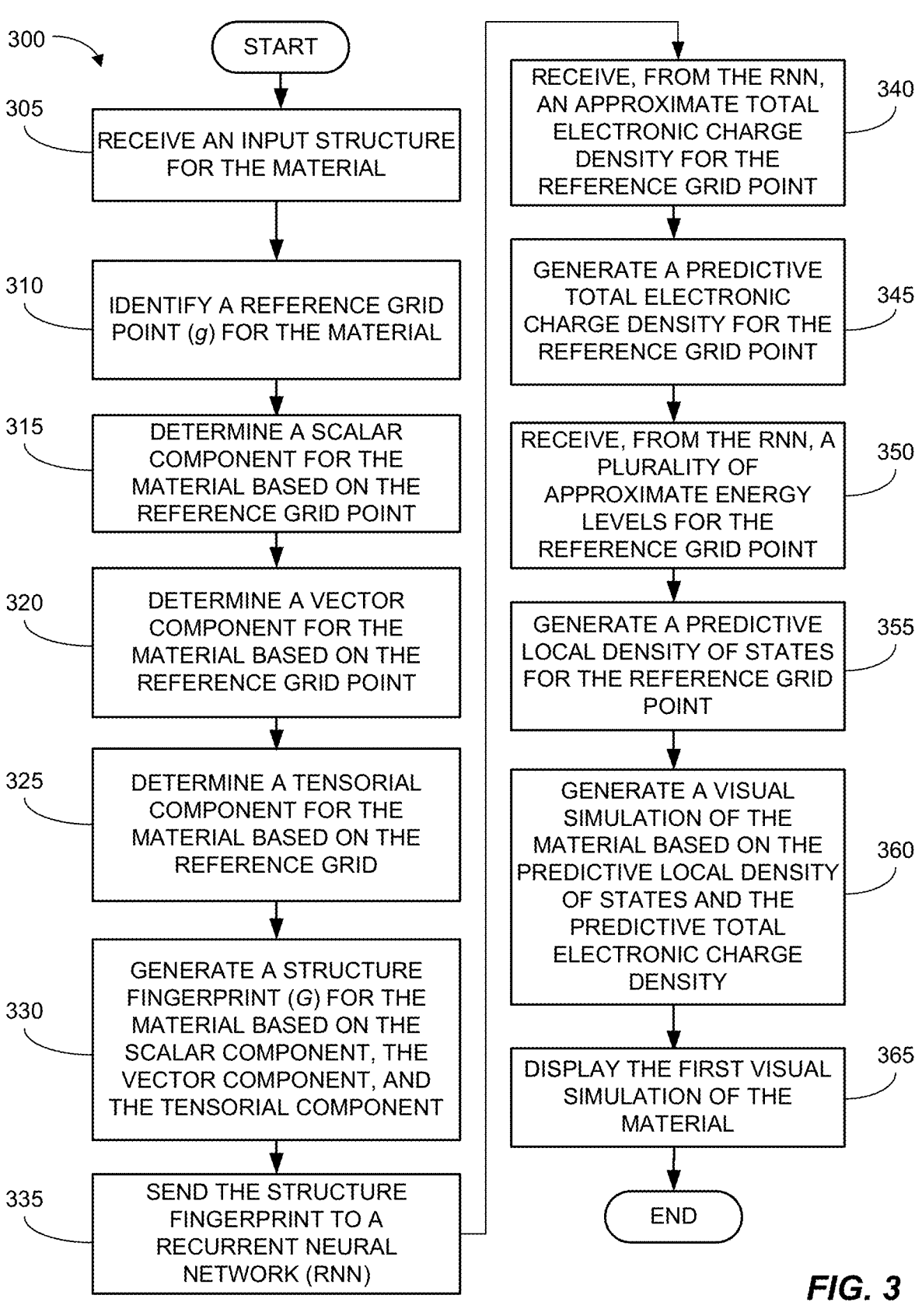

300

START

305 — RECEIVE AN INPUT STRUCTURE FOR THE MATERIAL

310 — IDENTIFY A REFERENCE GRID POINT (g) FOR THE MATERIAL

315 — DETERMINE A SCALAR COMPONENT FOR THE MATERIAL BASED ON THE REFERENCE GRID POINT

320 — DETERMINE A VECTOR COMPONENT FOR THE MATERIAL BASED ON THE REFERENCE GRID POINT

325 — DETERMINE A TENSORIAL COMPONENT FOR THE MATERIAL BASED ON THE REFERENCE GRID

330 — GENERATE A STRUCTURE FINGERPRINT (G) FOR THE MATERIAL BASED ON THE SCALAR COMPONENT, THE VECTOR COMPONENT, AND THE TENSORIAL COMPONENT

335 — SEND THE STRUCTURE FINGERPRINT TO A RECURRENT NEURAL NETWORK (RNN)

340 — RECEIVE, FROM THE RNN, AN APPROXIMATE TOTAL ELECTRONIC CHARGE DENSITY FOR THE REFERENCE GRID POINT

345 — GENERATE A PREDICTIVE TOTAL ELECTRONIC CHARGE DENSITY FOR THE REFERENCE GRID POINT

350 — RECEIVE, FROM THE RNN, A PLURALITY OF APPROXIMATE ENERGY LEVELS FOR THE REFERENCE GRID POINT

355 — GENERATE A PREDICTIVE LOCAL DENSITY OF STATES FOR THE REFERENCE GRID POINT

360 — GENERATE A VISUAL SIMULATION OF THE MATERIAL BASED ON THE PREDICTIVE LOCAL DENSITY OF STATES AND THE PREDICTIVE TOTAL ELECTRONIC CHARGE DENSITY

365 — DISPLAY THE FIRST VISUAL SIMULATION OF THE MATERIAL

END

*FIG. 3*

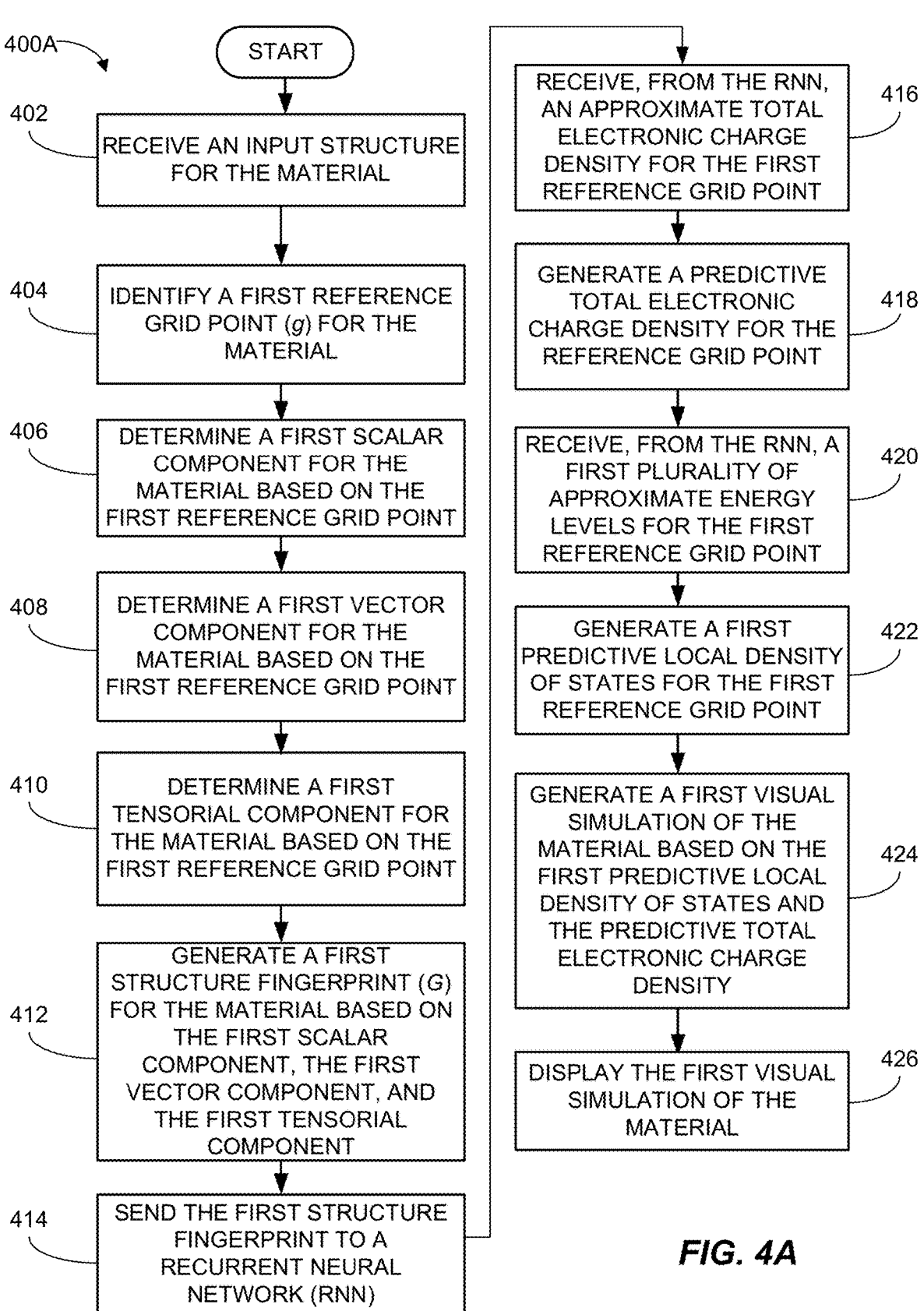

400A

START

402 — RECEIVE AN INPUT STRUCTURE FOR THE MATERIAL

404 — IDENTIFY A FIRST REFERENCE GRID POINT (g) FOR THE MATERIAL

406 — DETERMINE A FIRST SCALAR COMPONENT FOR THE MATERIAL BASED ON THE FIRST REFERENCE GRID POINT

408 — DETERMINE A FIRST VECTOR COMPONENT FOR THE MATERIAL BASED ON THE FIRST REFERENCE GRID POINT

410 — DETERMINE A FIRST TENSORIAL COMPONENT FOR THE MATERIAL BASED ON THE FIRST REFERENCE GRID POINT

412 — GENERATE A FIRST STRUCTURE FINGERPRINT (G) FOR THE MATERIAL BASED ON THE FIRST SCALAR COMPONENT, THE FIRST VECTOR COMPONENT, AND THE FIRST TENSORIAL COMPONENT

414 — SEND THE FIRST STRUCTURE FINGERPRINT TO A RECURRENT NEURAL NETWORK (RNN)

416 — RECEIVE, FROM THE RNN, AN APPROXIMATE TOTAL ELECTRONIC CHARGE DENSITY FOR THE FIRST REFERENCE GRID POINT

418 — GENERATE A PREDICTIVE TOTAL ELECTRONIC CHARGE DENSITY FOR THE REFERENCE GRID POINT

420 — RECEIVE, FROM THE RNN, A FIRST PLURALITY OF APPROXIMATE ENERGY LEVELS FOR THE FIRST REFERENCE GRID POINT

422 — GENERATE A FIRST PREDICTIVE LOCAL DENSITY OF STATES FOR THE FIRST REFERENCE GRID POINT

424 — GENERATE A FIRST VISUAL SIMULATION OF THE MATERIAL BASED ON THE FIRST PREDICTIVE LOCAL DENSITY OF STATES AND THE PREDICTIVE TOTAL ELECTRONIC CHARGE DENSITY

426 — DISPLAY THE FIRST VISUAL SIMULATION OF THE MATERIAL

*FIG. 4A*

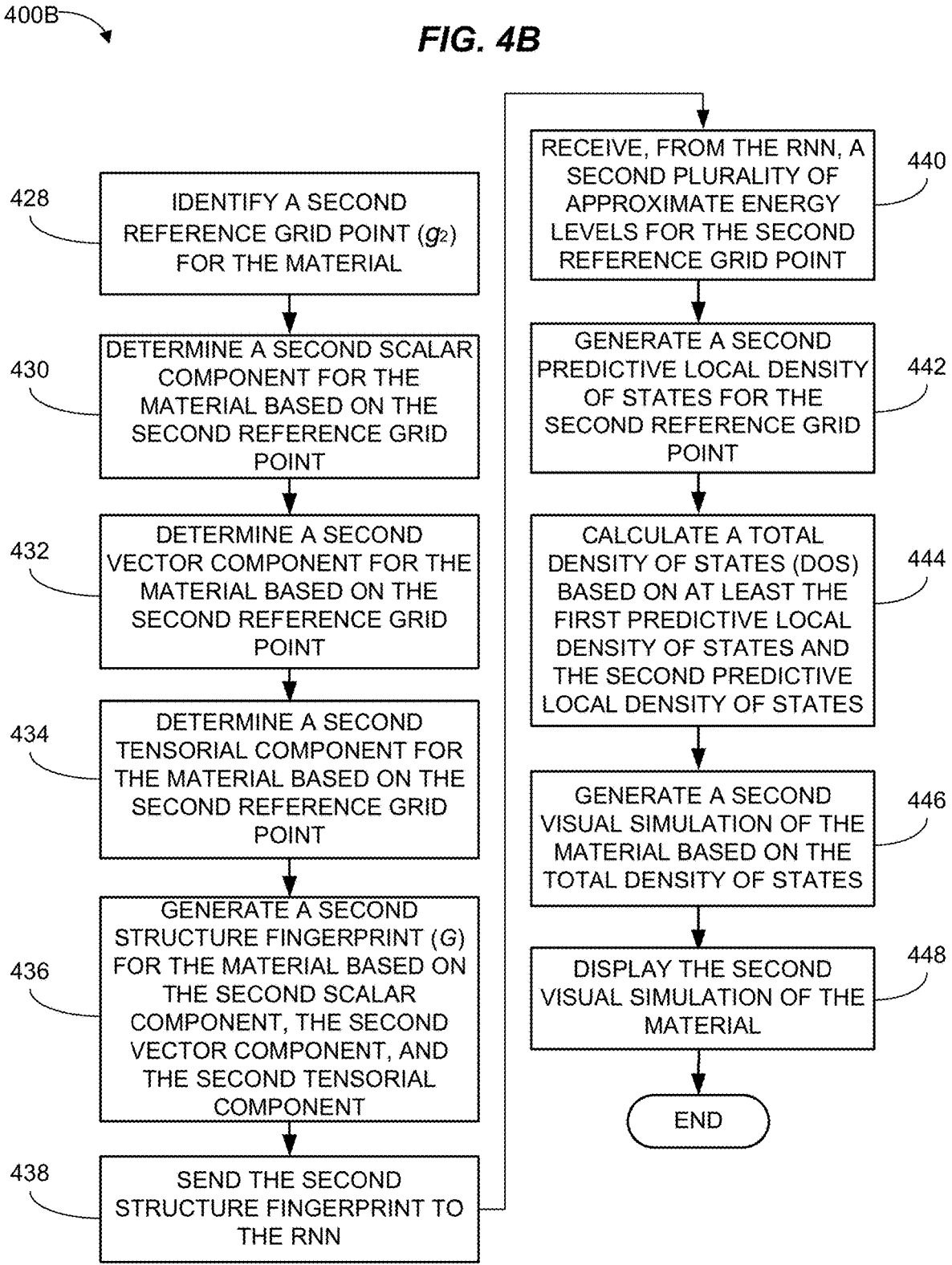

428 — IDENTIFY A SECOND REFERENCE GRID POINT ($g_2$) FOR THE MATERIAL

430 — DETERMINE A SECOND SCALAR COMPONENT FOR THE MATERIAL BASED ON THE SECOND REFERENCE GRID POINT

432 — DETERMINE A SECOND VECTOR COMPONENT FOR THE MATERIAL BASED ON THE SECOND REFERENCE GRID POINT

434 — DETERMINE A SECOND TENSORIAL COMPONENT FOR THE MATERIAL BASED ON THE SECOND REFERENCE GRID POINT

436 — GENERATE A SECOND STRUCTURE FINGERPRINT (G) FOR THE MATERIAL BASED ON THE SECOND SCALAR COMPONENT, THE SECOND VECTOR COMPONENT, AND THE SECOND TENSORIAL COMPONENT

438 — SEND THE SECOND STRUCTURE FINGERPRINT TO THE RNN

440 — RECEIVE, FROM THE RNN, A SECOND PLURALITY OF APPROXIMATE ENERGY LEVELS FOR THE SECOND REFERENCE GRID POINT

442 — GENERATE A SECOND PREDICTIVE LOCAL DENSITY OF STATES FOR THE SECOND REFERENCE GRID POINT

444 — CALCULATE A TOTAL DENSITY OF STATES (DOS) BASED ON AT LEAST THE FIRST PREDICTIVE LOCAL DENSITY OF STATES AND THE SECOND PREDICTIVE LOCAL DENSITY OF STATES

446 — GENERATE A SECOND VISUAL SIMULATION OF THE MATERIAL BASED ON THE TOTAL DENSITY OF STATES

448 — DISPLAY THE SECOND VISUAL SIMULATION OF THE MATERIAL

END

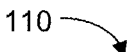
FIG. 5

SYSTEMS AND METHODS FOR MATERIAL SIMULATION

CROSS-REFERENCE TO RELATED APPLICATION

This application claims the benefit of, and priority under 35 U.S.C. § 119(e) to, U.S. Provisional Patent Application No. 62/744,593, entitled "Ultrafast Machine Learning Algorithm to Perform Materials Simulations with Quantum Mechanics," filed Oct. 11, 2018, the contents of which are hereby incorporated by reference herein in their entirety as if fully set forth below.

STATEMENT REGARDING FEDERALLY SPONSORED RESEARCH

This invention was made with government support under Grant No. N00014-17-1-2656 awarded by the Office of Naval Research. The government has certain rights in the invention.

FIELD OF THE INVENTION

The presently disclosed subject matter relates generally to systems and methods for material simulation and, more particularly, to systems and methods for fingerprinting a material and predicting the electronic structure of the material.

BACKGROUND

The electronic charge density distribution $\rho(r)$ of a given material is among the most fundamental quantities in quantum simulations from which many large-scale properties and observables can be calculated. Conventionally, $\rho(r)$ is obtained using Kohn-Sham density functional theory (KS-DFT) based methods. However, KS-DFT typically is limited to a few hundred atoms and has a high computational cost. Thus, KS-DFT is intractable for systems involving thousands/millions of atoms. While these limitations exist, current technology (e.g., machine learning) has improved, such that calculations based on the KS-DFT method may be used to more accurately and quickly predict the electronic structure of a large amount (e.g., millions) of atoms with less computational costs.

Accordingly, the present application is directed to an improved system and method for providing material simulation.

SUMMARY

Aspects of the disclosed technology include systems and methods for material simulation. Consistent with the disclosed embodiments, the methods may include the use of one or more processors, transceivers, computing devices, or graphical user interfaces. One exemplary method may include fingerprinting a material. The method may include receiving an input structure for the material and identifying a first reference grid point (g) for the material. Next, the method may include determining a first scalar component for the material that may comprise radial information of a plurality of atoms of the material. Also, the method may determine a first tensorial component and a first vector component for the material based on the first reference grid point. The method may also include generating a first structure fingerprint (G) for the material based on the first scalar component, the first vector component, and/or the first tensorial component. The first structure fingerprint may comprise a numerical representation of the first structure fingerprint. The method may further include sending the first structure fingerprint to a recurrent neural network (RNN) that maps the first structure fingerprint to stored atomic configurations.

In some examples, determining the first scalar component for the material may include applying an equation of:

$$S_{k\Omega} = c_k \sum\nolimits_{i=1}^{N_\Omega} \exp\left(\frac{-r_{gi}^2}{2\sigma_k^2}\right) f_c\left(r_{gi}\right),$$

wherein: $r_{gi}$ is an amount of distance between an atom (i) of a species $\Omega$, the first reference grid point location $g \cdot f_c(r_{gi})$ is any cutoff function that decays to zero for the plurality of atoms at a distance greater than $R_c$ from the first reference grid point such as $$.5\left[\cos\left(\frac{\pi r_{gi}}{R_c}\right)+1\right],$$

$c_k$ is a normalization constant given by $$\frac{1}{\sqrt{2\pi}\sigma_k},$$

$N_\Omega$ is a number of atoms of the species $\Omega$, and an overall dimensionality of the scalar component is product of a number of Gaussians k and a type of the species $\Omega$.

In some examples, determining the first vector component for the material may include applying an equation of:

$$V_{k\Omega}^{\alpha} = c_k \sum\nolimits_{i=1}^{N_\Omega} \frac{r_{gi}^\alpha}{r_{gi}} \exp\left(\frac{-r_{gi}^2}{2\sigma_k^2}\right) f_c\left(r_{gi}\right),$$

wherein $\alpha$ represents each of the x, y, or z directions.

According to some examples, the first vector component may be rendered rotationally invariant by applying an equation of: $V_{k\Omega} = \sqrt{(V_{k\Omega}^x)^2 + (V_{k\Omega}^y)^2 + (V_{k\Omega}^z)^2}$.

In some examples, determining the first tensorial component for the material may include applying an equation of:

$$T_{k\Omega}^{\alpha\beta} = c_k \sum\nolimits_{i=1}^{N_\Omega} \frac{r_{gi}^\alpha r_{gi}^\beta}{r_{gi}^2} \exp\left(\frac{-r_{gi}^2}{2\sigma_k^2}\right) f_c(r_{gi}),$$

wherein $\alpha$ represents each of the x, y, or z directions, and $\beta$ represents each of the x, y, or z directions.

In some examples, the first tensorial component may be rendered rotationally invariant by applying an equation of: $T'_{k\Omega} = T_{k\Omega}^{xx} T_{k\Omega}^{yy} + T_{k\Omega}^{yy} T_{k\Omega}^{zz} + T_{k\Omega}^{xx} T_{k\Omega}^{zz} - (T_{k\Omega}^{xy})^2 - (T_{k\Omega}^{yz})^2 - (T_{k\Omega}^{zx})^2$, and applying an equation of: $T''_{k\Omega} = \det T_{k\Omega}^{\alpha\beta}$.

In some examples, the first tensorial component may be rendered rotationally invariant by applying an equation of: $T'''_{k\Omega} = T_{k\Omega}^{xx} + T_{k\Omega}^{yy} + T_{k\Omega}^{zz}$.

According to some examples, the first structure fingerprint may be generated by applying an equation of: $G_{k\theta\phi}{}^n = \{M_\phi{}^n(S_{k\phi}); M_\phi{}^n(V_{k\phi}); M_\phi{}^n(T_{k\phi})\}$, wherein the first scalar component, the first vector component, and the first tensorial component are represented as $M^n$.

In some examples, the RNN may be located on a remote device.

In some examples, the RNN may include a plurality of hidden layers.

In some examples, each of the three hidden layers may include a plurality of neurons.

In some examples, the method may include receiving, from the RNN, an approximate total electronic charge density for the first reference grid point based on at least one corresponding stored atomic configuration, and generating a predictive total electronic charge density for the first reference grid point based on the approximate total electronic charge density.

According to some examples, the method may include receiving, from the RNN, a first plurality of approximate energy levels for the first reference grid point based on at least one corresponding stored atomic configuration, and generating a first predictive local density of states for the first reference grid point based on the first plurality of approximate energy levels.

In some examples, the method may include generating a visual simulation of the material based on the first predictive local density of states and the predictive total electronic charge density.

In some examples, the method may include sending instructions to a remote device that causes the remote device to display the visual simulation as a graphical user interface.

According to some examples, the method may further include: identifying a second reference grid point ($g_2$) for the material; determining a second scalar component, a second vector component, and a second tensorial component for the material based on the second reference grid point; generating a second structure fingerprint ($G_2$) for the material based on the second scalar component, the second vector component, and the second tensorial component; sending the second structure fingerprint to the RNN; receiving, from the RNN, a second plurality of approximate energy levels for the second reference grid point based on at least one corresponding stored atomic configuration; generating a second predictive local density of states for the second reference grid point based on the second plurality of approximate energy levels; and calculating a total density of states (DOS) based on at least the first predictive local density of states and the second predictive local density of states.

In some examples, determining the second scalar component for the material may further include applying an equation of:

$$S_{k\Omega} = c_k \sum_{i=1}^{N_\Omega} \exp\left(\frac{-r_{gi}^2}{2\sigma_k^2}\right) f_c\left(r_{g_2i}\right),$$

where $r_{g_2i}$ is an amount of distance between an atom (i) of a species $\Omega$, the second reference grid point location $g_2 \cdot f_c(r_{g_2i})$ is any cutoff function that decays to zero for the plurality of atoms at a distance greater than $R_c$ from the second reference grid point such as $$.5\left[\cos\left(\frac{\pi r_{g_2i}}{R_c}\right) + 1\right],$$

$c_k$ is a normalization constant given by $$\frac{1}{\sqrt{2\pi}\sigma_k},$$

$N_\Omega$ is a number of atoms of the species $\Omega$, and an overall dimensionality of the scalar component is product of a number of Gaussians k and a type of the species $\Omega$.

In some examples, determining the second vector component for the material may further include applying an equation of:

$$V_{k\Omega}^\alpha = c_k \sum_{i=1}^{N_\Omega} \frac{r_{g_2i}^\alpha}{r_{g_2i}} \exp\left(\frac{-r_{g_2i}^2}{2\sigma_k^2}\right) f_c\left(r_{g_2i}\right),$$

where $\alpha$ represents each of the x, y, or z directions.

In some examples, the method may include rendering the second vector component rotationally invariant by applying an equation of: $V_{k\Omega} = \sqrt{(V_{k\Omega}^x)^2 + (V_{k\Omega}^y)^2 + (V_{k\Omega}^z)^2}$.

In some examples, determining the second tensorial component for the material may further include applying an equation of:

$$T_{k\Omega}^{\alpha\beta} = c_k \sum_{i=1}^{N_\Omega} \frac{r_{g_2i}^\alpha r_{g_2i}^\beta}{r_{g_2i}^2} \exp\left(\frac{-r_{g_2i}^2}{2\sigma_k^2}\right) f_c\left(r_{g_2i}\right),$$

where $\alpha$ represents each of the x, y, or z directions, and $\beta$ represents each of the x, y, or z directions.

In some examples, the method may include rendering the second tensorial component rotationally invariant by applying an equation of: $T'_{k\Omega} = T_{k\Omega}^{xx}T_{k\Omega}^{yy} + T_{k\Omega}^{yy}T_{k\Omega}^{zz} + T_{k\Omega}^{xx}T_{k\Omega}^{zz} - (T_{k\Omega}^{xy})^2 - (T_{k\Omega}^{yz})^2 - (T_{k\Omega}^{zx})^2$, and applying an equation of: $T''_{k\Omega} = \det T_{k\Omega}^{\alpha\beta}$.

In some examples, the method may include rendering the second tensorial component rotationally invariant by applying an equation of: $T'''_{k\Omega} = T_{k\Omega}^{xx} + T_{k\Omega}^{yy} + T_{k\Omega}^{zz}$.

According to some examples, generating the second structure fingerprint may further include applying an equation of: $G_{k\Theta\phi}^n = \{M_\phi^n(S_{k\phi}); M_\phi^n(V_{k\phi}); M_\phi^n(T_{k\phi})\}$, wherein the second scalar component, the second vector component, and the second tensorial component are represented as $M^n$.

In some examples, the method may further include generating a visual simulation of the material based on the total density of states and the predictive total electronic charge density.

In some examples, the method may further include displaying, by a graphical user interface, the visual simulation of the material.

In some examples, the method may further include sending instructions to a remote device that causes the remote device to display the visual simulation as a graphical user interface.

One exemplary system for material simulation may include a processor, a transceiver, a recurrent neural network (RNN), a graphical user interface and memory in communication with the processor, the transceiver, the RNN, and the graphical user interface. The memory may store instructions, that when executed cause the system to: receive an input structure for the material; identify a first reference grid point (g) for the material; determine a first scalar component, a first vector component, and a first tensorial component for the material based on the first reference grid point; render the first vector component and the first tensorial component rotationally invariant; generate a first structure fingerprint (G) for the material, that is a numerical representation of the first structure fingerprint, based on the first scalar component, the first vector component, and the first tensorial component; map the first structure fingerprint to stored atomic configurations; determine an approximate total electronic charge density for the first reference grid point based on at least one corresponding stored atomic configuration; determine a predictive total electronic charge density for the first reference grid point based on the approximate total electronic charge density; determine a first plurality of approximate energy levels for the first reference grid point based on at least one corresponding stored atomic configuration; determine a first predictive local density of states for the first reference grid point based on the first plurality of approximate energy levels; generate a first visual simulation of the material based on the first predictive local density of states and the predictive total electronic charge density; and display the first visual simulation of the material.

In some examples, the system may determine the first scalar component for the material may include applying an equation of:

$$S_{k\Omega} = c_k \sum_{i=1}^{N_\Omega} \exp\left(\frac{-r_{gi}^2}{2\sigma_k^2}\right) f_c\,(r_{gi}),$$

where $r_{gi}$ is an amount of distance between an atom (i) of a species $\Omega$, the first reference grid point location $g \cdot f_c(r_{gi})$ is any cutoff function that decays to zero for the plurality of atoms at a distance greater than $R_c$ from the first reference grid point such as $$.5\left[\cos\left(\frac{\pi r_{gi}}{R_c}\right) + 1\right],$$

$c_k$ is a normalization constant given by $$\frac{1}{\sqrt{2\pi}\sigma_k},$$

$N_\Omega$ is a number of atoms of the species $\Omega$, and an overall dimensionality of the scalar component is product of a number of Gaussians k and a type of the species $\Omega$.

In some examples, the system may determine the first vector component for the material may include applying an equation of:

$$v_{k\Omega}^\alpha = c_k \sum_{i=1}^{N_\Omega} \frac{r_{gi}^\alpha}{r_{gi}} \exp\left(\frac{-r_{gi}^2}{2\sigma_k^2}\right) f_c\,(r_{gi}),$$

wherein $\alpha$ represents each of the x, y, or z directions.

According to some examples, the first vector component may be rendered rotationally invariant by applying an equation of: $V_{k\Omega} = \sqrt{(V_{k\Omega}^x)^2 + (V_{k\Omega}^y)^2 + (V_{k\Omega}^z)^2}$.

In some examples, the system may determine the first tensorial component for the material may include applying an equation of:

$$T_{k\Omega}^{\alpha\beta} = c_k \sum_{i=1}^{N_\Omega} \frac{r_{gi}^\alpha r_{gi}^\beta}{r_{gi}^2} \exp\left(\frac{-r_{gi}^2}{2\sigma_k^2}\right) f_c\,(r_{gi}),$$

wherein $\alpha$ represents each of the x, y, or z directions, and $\beta$ represents each of the x, y, or z directions.

In some examples, the first tensorial component may be rendered rotationally invariant by applying an equation of: $T'_{k\Omega} = T_{k\Omega}^{xx} T_{k\Omega}^{yy} + T_{k\Omega}^{yy} T_{k\Omega}^{zz} + T_{k\Omega}^{xx} T_{k\Omega}^{zz} - (T_{k\Omega}^{xy})^2 - (T_{k\Omega}^{yz})^2 - (T_{k\Omega}^{zx})^2$, and applying an equation of: $T''_{k\Omega} = \det T_{k\Omega}^{\alpha\beta}$.

In some examples, the first tensorial component may be rendered rotationally invariant by applying an equation of: $T'''_{k\Omega} = T_{k\Omega}^{xx} + T_{k\Omega}^{yy} + T_{k\Omega}^{zz}$.

According to some examples, the system may generate the first structure fingerprint by applying an equation of: $G_{kg\phi}'' = \{M_\phi''(S_{k\phi}); M_\phi''(V_{k\phi}); M_\phi''(T_{k\phi})\}$, wherein the first scalar component, the first vector component, and the first tensorial component are represented as $M''$.

According to some examples, the system may further: identify a second reference grid point ($g_2$) for the material; determine a second scalar component, a second vector component, and a second tensorial component for the material based on the second reference grid point; generate a second structure fingerprint ($G_2$) for the material based on the second scalar component, the second vector component, and the second tensorial component; map the second structure fingerprint to stored atomic configurations; determine a second plurality of approximate energy levels for the second reference grid point based on at least one corresponding stored atomic configuration; determine a second predictive local density of states for the second reference grid point based on the second plurality of approximate energy levels; and calculate a total density of states (DOS) based on at least the first predictive local density of states and the second predictive local density of states.

In some examples, the system may generate a second visual simulation of the material based on the total density of states.

In some examples, the system may display the second visual simulation of the material.

In some examples, the system may send instructions to a remote device that causes the remote device to display the second visual simulation as a graphical user interface.

In some examples, the system may determine the second scalar component for the material by applying an equation of:

$$S_{k\Omega} = c_k \sum_{i=1}^{N_\Omega} \exp\left(\frac{-r_{g2i}^2}{2\sigma_k^2}\right) f_c\,(r_{g2i}),$$

wherein: $r_{g2i}$ is an amount of distance between an atom (i) of a species $\Omega$, the second reference grid point location $g_2 \cdot f_c(T_{g2i})$ is any cutoff function that decays to zero for the plurality of atoms at a distance greater than $R_c$ from the second reference grid point such as $$.5\left[\cos\left(\frac{\pi r_{g2i}}{R_c}\right) + 1\right],$$

$c_k$ is a normalization constant given by $$\frac{1}{\sqrt{2\pi}\sigma_k},$$

$N_{\Omega}$ is a number of atoms of the species $\Omega$, and an overall dimensionality of the scalar component is product of a number of Gaussians k and a type of the species $\Omega$.

In some examples, the system may determine the second vector component for the material by applying an equation of:

$$V_{k\Omega}^{\alpha} = c_k \sum\nolimits_{i=1}^{N_{\Omega}} \frac{r_{g2i}^{\alpha}}{r_{g2i}} \exp\left(\frac{-r_{g2i}^2}{2\sigma_k^2}\right) f_c\left(r_{g2i}\right),$$

wherein $\alpha$ represents each of the x, y, or z directions.

In some examples, the system may render the second vector component rotationally invariant by applying an equation of: $V_{k\Omega} = \sqrt{(V_{k\Omega}^x)^2 + (V_{k\Omega}^y)^2 + (V_{k\Omega}^z)^2}$.

In some examples, the system may determine the second tensorial component for the material may further include applying an equation of:

$$T_{k\Omega}^{\alpha\beta} = c_k \sum\nolimits_{i=1}^{N_{\Omega}} \frac{r_{g2i}^{\alpha} r_{g2i}^{\beta}}{r_{g2i}^2} \exp\left(\frac{-r_{g2i}^2}{2\sigma_k^2}\right) f_c\left(r_{g2i}\right),$$

wherein: $\alpha$ represents each of the x, y, or z directions, and $\beta$ represents each of the x, y, or z directions.

In some examples, the system may render the second tensorial component rotationally invariant by applying an equation of: $T'_{k\Omega} = T_{k\Omega}^{xx} T_{k\Omega}^{yy} + T_{k\Omega}^{yy} T_{k\Omega}^{zz} + T_{k\Omega}^{xx} T_{k\Omega}^{zz} - (T_{k\Omega}^{xy})^2 - (T_{k\Omega}^{yz})^2 - (T_{k\Omega}^{zx})^2$, and applying an equation of: $T''_{k\Omega} = \det T_{k\Omega}^{\alpha\beta}$.

In some examples, the system may render the second tensorial component rotationally invariant by applying an equation of: $T'''_{k\Omega} = T_{k\Omega}^{xx} + T_{k\Omega}^{yy} + T_{k\Omega}^{zz}$.

According to some examples, the system may generate the second structure fingerprint may further include applying an equation of: $G_{2_{k\Omega\phi}}^{n} = \{M_{\phi}^n(S_{k\phi}); M_{\phi}^n(V_{k\phi}); M_{\phi}^n(T_{k\phi})\}$, wherein the second scalar component, the second vector component, and the second tensorial component are represented as $M^n$.

Further features of the disclosed design, and the advantages offered thereby, are explained in greater detail hereinafter with reference to specific embodiments illustrated in the accompanying drawings, wherein like elements are indicated be like reference designators.

BRIEF DESCRIPTION OF THE DRAWINGS

Reference will now be made to the accompanying drawings, which are not necessarily drawn to scale, are incorporated into and constitute a portion of this disclosure, illustrate various implementations and aspects of the disclosed technology, and, together with the description, serve to explain the principles of the disclosed technology. In the drawings:

FIG. 2 is an example flow chart of a method for fingerprinting a material, in accordance with some examples of the present disclosure;

FIG. 3 is an example flow chart of a method for simulating a material, in accordance with some examples of the present disclosure;

FIGS. 4A-B are example flow charts of a method for simulating a material, in accordance with some examples of the present disclosure;

FIG. 5 is a component diagram of an example of a computing device, in accordance with some examples of the present disclosure.

DETAILED DESCRIPTION

Some implementations of the disclosed technology will be described more fully with reference to the accompanying drawings. This disclosed technology can be embodied in many different forms, however, and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein can include, but are not limited to, for example, components developed after development of the disclosed technology.

It is also to be understood that the mention of one or more method steps does not imply that the methods steps must be performed in a particular order or preclude the presence of additional method steps or intervening method steps between the steps expressly identified.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

Figure 1:
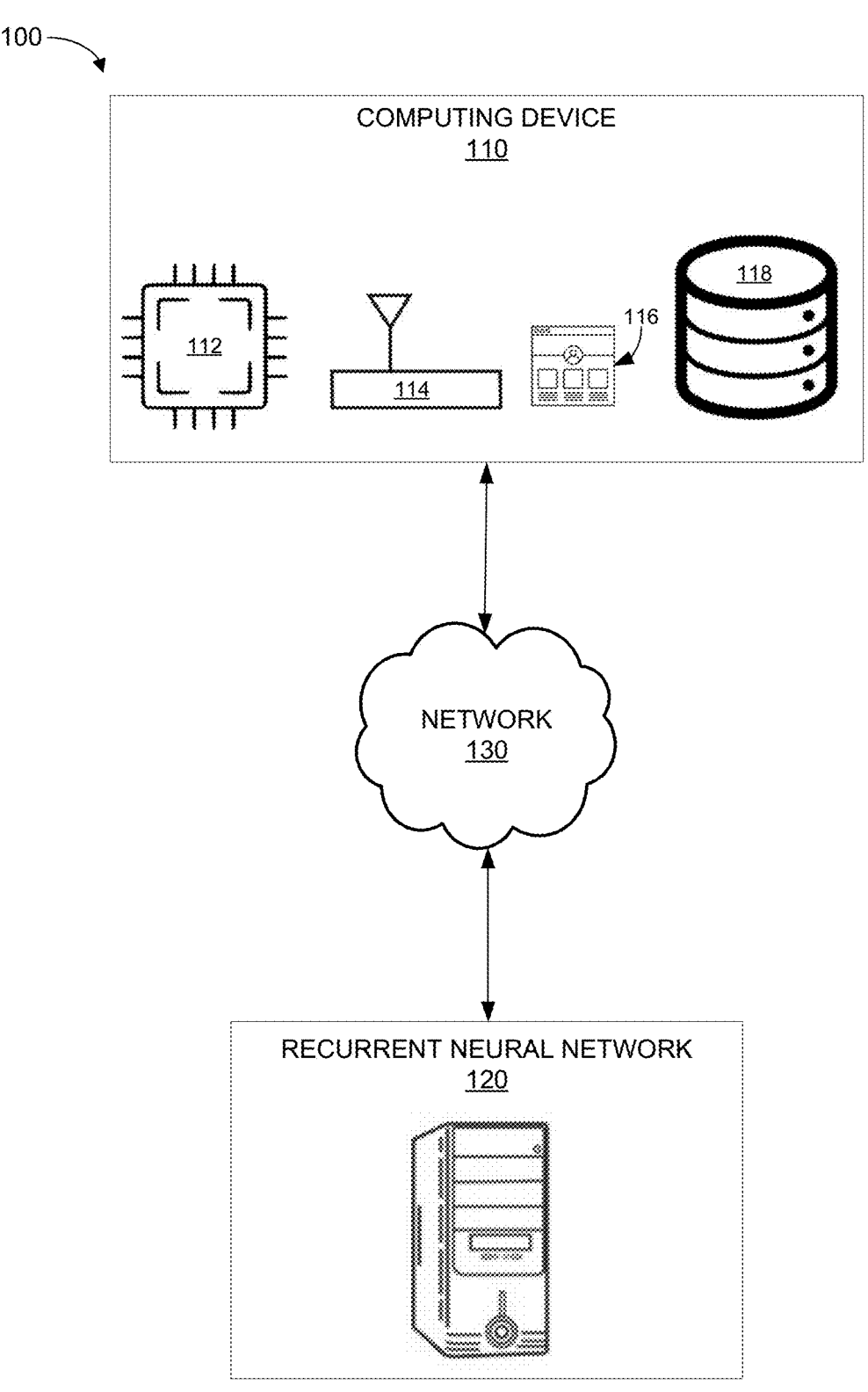
FIG. 1 is a diagram of an example system for fingerprinting and simulating a material, in accordance with some examples of the present disclosure.

FIG. 1 shows an example system 100 that may be used for fingerprinting and simulating a material. The components and arrangements shown in FIG. 1 are not intended to limit the disclosed embodiments as the components used to implement the disclosed processes and features may vary. As shown in FIG. 1, in some implementations the system 100 includes a recurrent neural network (RNN) 120, a network 130, and a computing device 110, which may include one or more processors 112, a transceiver 114, a graphical user interface 116, and a database 118.

As non-limiting examples, the network 130 may include a network of interconnected computing devices such as a local area network (LAN), Wi-Fi, Bluetooth, or other type of network and may be connected to an intranet or the Internet, among other things. The computing device 110 may include one or more physical or logical devices (e.g., servers) or drives and may be implemented as a single server or a bank of servers (e.g., in a "cloud"). The RNN 120 can include instructions and or/memory used to perform certain features disclosed herein. The RNN 120 may be part of the computing device 110 or may be comprise a separate device in communication with the computing device 110. An example computer architecture that may be used to implement the computing device 110 is described below with reference to FIG. 5.

The computing device 110 may perform fingerprinting of a material—i.e., generating a numerical representation of the atomic arrangement around a grid point of the material. The computing device 110 may generate fingerprint structure for a material (or a molecule (e.g., aluminum)) and then use the fingerprint structure to generate a simulation of the material. The computing device 110 may receive an input structure for the material. The input structure may be a text file containing the cartesian coordinates, types of each atom, and/or vectors that define the dimensions and shape of a unit cell within which the atoms reside. Next, the computing device 110 may identify a first reference grid point (g) for the material, which may include an arrangement of atoms of the material. To generate the fingerprint structure (a numerical representation of the atomic arrangement around a grid point), the computing device 110 may determine a first scalar component, a first vector component, and a first tensorial component for the material based on the first reference grid point. The scalar component may comprise radial information of a plurality of atoms of the material.

To determine the first scalar component for the material, the computing device 110 may execute an algorithm that applies an equation of:

$$S_{k\Omega} = c_k \sum_{i=1}^{N_\Omega} \exp\left(\frac{-r_{gi}^2}{2\sigma_k^2}\right) f_c(r_{gi}).$$

In the aforementioned equation, $r_{gi}$ is an amount of distance between an atom (i) of a species $\Omega$, the first reference grid point location $g \cdot f_c(r_{gi})$ is any cutoff function that decays to zero for the plurality of atoms at a distance greater than $R_c$ from the first reference grid point such as $$.5\left[\cos\left(\frac{\pi r_{gi}}{R_c}\right) + 1\right],$$

$c_k$ is a normalization constant given by $$\frac{1}{\sqrt{2\pi}\sigma_k},$$

$N_\Omega$ is a number of atoms of the species $\Omega$, and an overall dimensionality of the scalar component is product of a number of Gaussians k and a type of the species $\Omega$.

The computing device 110 may further determine the first vector component for the material by executing an algorithm that applies an equation of:

$$v_{k\Omega}^\alpha = c_k \sum_{i=1}^{N_\Omega} \frac{r_{gi}^\alpha}{r_{gi}^2} \exp\left(\frac{-r_{gi}^2}{2\sigma_k^2}\right) f_c(r_{gi}),$$

where $\alpha$ represents each of the x, y, or z directions.

Also, the computing device 110 may determine the first tensorial component for the material by executing an algorithm that applies an equation of:

$$T_{k\Omega}^{\alpha\beta} = c_k \sum_{i=1}^{N_\Omega} \frac{r_{gi}^\alpha r_{gi}^\beta}{r_{gi}^2} \exp\left(\frac{-r_{gi}^2}{2\sigma_k^2}\right) f_c(r_{gi}),$$

where $\alpha$ represents each of the x, y, or z directions, and $\beta$ represents each of the x, y, or z directions.

To ensure that the generated first fingerprint structure is invariant to system translation, rotation and permutations of atoms, the computing device 110 may render the first vector component and the first tensorial component rotationally invariant. The computing device 110 may render the first vector component rotationally invariant by executing an algorithm that applies an equation of: $V_{k\Omega} = \sqrt{(V_{k\Omega}^x)^2 + (V_{k\Omega}^y)^2 + (V_{k\Omega}^z)^2}$.

Similarly, the computing device 110 may render the first tensorial component rotationally invariant by executing the algorithm that applies an equation of: $T'_{k\Omega} = T_{k\Omega}^{xx} T_{k\Omega}^{yy} + T_{k\Omega}^{yy} T_{k\Omega}^{zz} + T_{k\Omega}^{xx} T_{k\Omega}^{zz} - (T_{k\Omega}^{xy})^2 - (T_{k\Omega}^{yz})^2 - (T_{k\Omega}^{zx})^2$, and applies an equation of: $T''_{k\Omega} = \det T_{k\Omega}^{\alpha\beta}$.

Additionally or alternatively, the computing device 110 may render the first tensorial component rotationally invariant by executing the algorithm that applies an equation of: $T'''_{k\Omega} = T_{k\Omega}^{xx} + T_{k\Omega}^{yy} + T_{k\Omega}^{zz}$.

Based on the first scalar component, the first vector component, and the first tensorial component, the computing device 110 may generate the first structure fingerprint (G), which may be accomplished by executing the algorithm that applies an equation of: $G_{k\Theta\phi}^n = \{M_\phi^n(S_{k\phi}); M_\phi^n(V_{k\phi}); M_\phi^n(T_{k\phi})\}$, where the first scalar component, the first vector component, and the first tensorial component are represented as $M^n$.

Next, the computing device 110 may send the first structure fingerprint to the RNN 120. The RNN 120 may map the first structure fingerprint to stored atomic configurations, for example, standard DFT calculations at that point. In some examples, the RNN 120 may be a deep feed forward neural network (DNN). The RNN 120 may include a set of layers of neurons, namely, an input-layer, hidden layers, and/or an output layer. In the input layer, each neuron may contain a component of the first fingerprint structure and the size of the input-layer may be decided by the number of components in the first fingerprint structure. In the hidden layers, each neuron may represent a pre-defined parametrized function acted upon by a weighted linear transform of each of the neurons in the previous layer. The number of neurons in each hidden layer and number of hidden layers may be hyper parameters chosen and/or optimized based on the material. The RNN 120 may determine the underlying functional relationship between the first fingerprint structure and the property may be learned by finding the correct weights of the linear transforms and the function parameters used in each neuron by an optimization algorithm.

The RNN 120 may determine an approximate total electronic charge density for the first reference grid point based on at least one corresponding stored atomic configuration, which may be sent to the computing device 110. Further, the RNN 120 may determine a first plurality of approximate energy levels for the first reference grid point based on at least one corresponding stored atomic configuration, which may also be sent to the computing device 110.

Turning back to the computing device 110, after receiving the approximate total electronic charge density for the first reference grid point, the computing device 110 may generate a predictive total electronic charge density for the first reference grid point based on the approximate total electronic charge density. Also, after receiving the first plurality of approximate energy levels for the first reference grid point, the computing device 110 may generate a first predictive local density of states for the first reference grid point based on the first plurality of approximate energy levels. The computing device 110 may then generate a first visual simulation of the material based on the first predictive local density of states and the predictive total electronic charge density, which may be displayed by the graphical user interface 116.

To calculate a total density of states (DOS), the computing device may identify a second reference grid point for the material and generate a second structure fingerprint in a similar or same manner as described above in reference to the first reference grid. More explicitly, once the computing device 110 identifies the second reference grid point, the computing device 110 may determine a second scalar component, a second vector component, and a second tensorial component based on the second reference grid point. The computing device 110 may determine the second scalar component, the second vector component, and the second tensorial by executing the algorithm that applies the corresponding equation described above for the first scalar component, the first vector component, and the first tensorial component, respectively with $g_2$ in place of g. Similar to the equations described above, the computing device 110 may execute the algorithm to apply the equation for rendering the first vector component invariant to the second vector component with $g_2$ in place of g, and may apply the equation(s) for rendering the first tensorial component invariant to the second tensorial component with $g_2$ in place of g.

The computing device 110 may then generate the second structure fingerprint ($G_2$) for the material based on the second scalar component, the second vector component, and the second tensorial component. As with the first structure fingerprint, the second structure fingerprint may be a numerical representation of the second structure fingerprint. Next, the computing device 110 may send the second structure fingerprint to the RNN 120 that maps the second structure fingerprint to stored atomic configurations to determine a second plurality of approximate energy levels for the second reference grid point. Then, based on the second plurality of approximate energy levels, the computing device 110 may generate a second predictive local density of states for the second reference grid point. Further, the computing device 110 may calculate a total density of states (DOS) based on at least the first predictive local density of states and the second predictive local density of states, which the computing device 110 may use to generate a second visual simulation of the material. Again, the graphical user interface 116 may display the second visual simulation of the material. In some examples, the computing device 110 may send instructions to a remote device (e.g., a server) that causes the remote device to display the first visual simulation and/or the second visual simulation as a graphical user interface.

FIG. 2 shows an example flow chart of a method for fingerprinting a material. The method 200 is illustrated from the perspective of the computing device 110, which may communicate with the RNN 120. The computing device 110 may determine a scalar component, a vector component, and a tensorial component to determine a structure fingerprint (numeric representation for the atomic arrangement around a grid point) for the material.

At 205, the computing device 110 may receive an input structure for a material or a molecule. At 210, the computing device 110 may identify a reference grid point for the material. The computing device 110 may determine a scalar component for material based on the reference grid point at 215. This may be accomplished by an algorithm executed by the computing device 110 that applies an equation $$S_{k\Omega} = c_k \sum\nolimits_{i=1}^{N_\Omega} \exp\left(\frac{-r_{gi}^2}{2\sigma_k^2}\right) f_c(r_{gi}),$$

where $r_{gi}$ is an amount of distance between an atom (i) of a species $\Omega$, the first reference grid point location $g \cdot f_c(r_{gi})$ is any cutoff function that decays to zero for the plurality of atoms at a distance greater than $R_c$ from the first reference grid point such as $$.5\left[\cos\left(\frac{\pi r_{gi}}{R_c}\right) + 1\right],$$

$c_k$ is a normalization constant given by $$\frac{1}{\sqrt{2\pi\sigma_k}},$$

$N_\Omega$ is a number of atoms of the species $\Omega$, and an overall dimensionality of the scalar component is product of a number of Gaussians k and a type of the species $\Omega$.

At 220, the computing device 110 may determine a vector component for the material based on the reference grid point by applying an equation of:

$$V_{k\Omega}^\alpha = c_k \sum\nolimits_{i=1}^{N_\Omega} \frac{r_{gi}^\alpha}{r_{gi}} \exp\left(\frac{-r_{gi}^2}{2\sigma_k^2}\right) f_c(r_{gi}),$$

where $\alpha$ represents each of the x, y, or z directions. Further, at 225, the computing device 110 may determine the tensorial component for the material based on the reference grid by applying an equation of:

$$T_{k\Omega}^{\alpha\beta} = c_k \sum\nolimits_{i=1}^{N_\Omega} \frac{r_{gi}^\alpha r_{gi}^\beta}{r_{gi}^2} \exp\left(\frac{-r_{gi}^2}{2\sigma_k^2}\right) f_c(r_{gi}),$$

where $\alpha$ represents each of the x, y, or z directions, and $\beta$ represents each of the x, y, or z directions.

In some examples, the computing device 110 may render the vector component and the tensorial component invariant by applying an equation mentioned above in reference to FIG. 1. At 230, the computing device 110 may generate a structure fingerprint (G) for the material based on the scalar component, the vector component, and first tensorial component, which may be accomplished by applying an equation of: $G_{k\theta\phi}{}^n = \{M_\phi{}^n(S_{k\phi}); M_\phi{}^n(V_{k\phi}); M_\phi{}^n(T_{k\phi})\}$, where the scalar component, the vector component, and the tensorial component are represented as $M^n$. At 235, the computing device 110 may send the structure fingerprint to the RNN 120, which may map the structure fingerprint to stored atomic configurations.

FIG. 3 is an example flow chart of a method for simulating a material. The method 300 may be performed by the computing device 110 in communication with the RNN 120. The computing device 110 may generate a structure fingerprint that is sent to the RNN 120, which sends information used to predict the local density of states and the total electronic charge density for the grid point.

Steps 305-335 may be the same or substantially similar to steps 205-235, as described in FIG. 2. The computing device 110 may perform the following for steps 305-335: receive an input structure for the material at 305; identify a reference grid point (g) for the material at 310; determine a scalar component for the material based on the reference grid point at 315; determine a vector component for the material based on the reference grid point at 320; determine a tensorial component for the material based on the reference grid point at 325; generate a structure fingerprint (G) for the material based on the scalar component, the vector component, and the tensorial component at 330; and send the structure fingerprint to the RNN 120 at 335.

At 340, the computing device 110 may receive, from the RNN 120, an approximate total electronic charge density for the reference grid point based on at least one corresponding stored atomic configuration. At 345, based on the approximate total electronic charge density, the computing device 110 may generate a predictive total electronic charge density for the reference grid point. At 350, the computing device 110 may receive, from the RNN 120, a plurality of approximate energy levels for the reference grid point based on at least one corresponding stored atomic configuration. At 355, the computing device 110 may generate a predictive local density of states for the first reference grid point based on the plurality of approximate energy levels. Based on the predictive local density of states and the predictive total electronic charge density, the computing device 110 may generate a visual simulation of the material at 360. Next, at 365, the computing device may display the visual simulation as the graphical user interface 116.

FIGS. 4A-B are other example flow charts of a method for simulating a material. The method 400A and 400B may be performed by the computing device 110 in communication with the RNN 120. Similar to method 300 described in FIG. 3, the computing device 110 may generate a structure fingerprint that is sent to the RNN 120, which sends information used to predict the local density of states and the total electronic charge density for the grid point. The method 400A and 400B may further identify a second reference grid point that is used to calculate a total density of states.

Steps 402-426 may be the same or substantially similar to steps 305-365, as described in FIG. 3. Steps 402-414 may include the computing device 110: receiving an input structure for the material at 402; identifying a first reference grid point (g) for the material at 404; determining a first scalar component for the material based on the first reference grid point at 406; determining a first vector component for the material based on the first reference grid point at 408; determining a first tensorial component for the material based on the first reference grid point at 410; generating a first structure fingerprint (G) for the material based on the first scalar component, the first vector component, and the first tensorial component at 412; sending the first structure fingerprint to the RNN 120 at 414; receiving, from the RNN 120, an approximate total electronic charge density for the first reference grid point based on at least one corresponding stored atomic configuration at 416; generating a predictive total electronic charge density for the first reference grid point based on the approximate total electronic charge density at 418; receiving, from the RNN 120, a first plurality of approximate energy levels for the first reference grid point based on at least one corresponding stored atomic configuration at 420; generating a first predictive local density of states for the first reference grid point based on the first plurality of approximate energy levels at 422; generating a first visual simulation of the material based on the first predictive local density of states and the predictive total electronic charge density at 424; and displaying, by the graphical user interface 116, the first visual simulation of the material at 426.

At 428, the computing device 110 may identify a second reference grid point ($g_2$) for the material. At 430, the computing device 110 may determine the second scalar component for component based on the second reference grid point by applying the corresponding equation described above in reference to determining the first scalar component with $g_2$ in place of g. Similarly, the computing device 110 may determine the second tensorial component at 432 and the second tensorial component, at 434, based on the second reference grid point. At 436, the computing device 110 may generate a second structure fingerprint ($G_2$) for the material based on the second scalar component, the second vector component, and the second tensorial component by applying an equation of: $G_{2_{k\theta\phi}}''=\{M_\phi''(S_{k\phi}); M_\phi''(V_{k\phi}); M_\phi''(T_{k\phi})\}$, where the second scalar component, the second vector component, and the second tensorial component are represented as M″.

At 438, the computing device 110 may send the second structure fingerprint to the RNN 120. At 440, the computing device 110 may receive, from the RNN 120, a second plurality of approximate energy levels for the second reference grid point based on at least one corresponding stored atomic configuration. At 442, the computing device 110 may generate a second predictive local density of states for the second reference grid point based on the second plurality of approximate energy levels. Next, at 444, the computing device 110 may calculate a total density of states (DOS) based on at least the first predictive local density of states and the second predictive local density of states. At 446, the computing device 110 may generate a second visual simulation of the material based on the total density of states, which may be displayed by the graphical user interface 116, at 448.

As shown in FIG. 5, the system 100 and methods 200, 300, 400A and 400B may be used in conjunction with the computing device 110. The computing device 110 may comprise, for example, a desktop or laptop computer, a server, bank of servers, or cloud-based server bank. Thus, while the computing device 110 is depicted as single standalone servers, other configurations or existing components could be used.

In various implementations, the memory 502 may be volatile (such as random-access memory (RAM)), nonvolatile (such as read only memory (ROM), flash memory, etc.), or some combination of the two. The memory 502 may include all, or part, of the functions of a simulation app 508, among other things. The memory 502 may also include the OS 510. Of course, the OS 510 varies depending on the manufacturer of the computing device 110 and the type of component. Many servers, for example, run Linux or Windows Server. The OS 510 contains the modules and software that supports a computer's basic functions, such as scheduling tasks, executing applications, and controlling peripherals.

The computing device 110 may also comprise one or more processors 516, which may include a central processing unit (CPU), a graphics processing unit (GPU), or both CPU and GPU, or any other sort of processing unit. The simulation app 508 may provide communication between the computing device 110 and the RNN 120. Thus, the simulation app 508 may send a first structure fingerprint and/or the second structure fingerprint to the RNN 120. Also, the simulation app 508 may receive an approximate total electronic charge density for the first reference grid point, a first plurality of approximate energy levels for the first reference grid point, and/or a second plurality of approximate energy levels for the second reference grid point.

The computing device 110 may also include additional data storage devices (removable and/or non-removable) such as, for example, magnetic disks, optical disks, or tape. Such additional storage is illustrated in FIG. 5 by removable storage 518 and non-removable storage 520. The removable storage 518 and non-removable storage 520 may store some, or all, of the OS 510 and functions 508.

Non-transitory computer-readable media may include volatile and nonvolatile, removable and non-removable tangible, physical media implemented in technology for storage of information, such as computer readable instructions, data structures, program modules, or other data. The memory 502, removable storage 518, and non-removable storage 520 are all examples of non-transitory computer-readable media. Non-transitory computer-readable media include, but are not limited to, RAM, ROM, EEPROM, flash memory or other memory technology, CD-ROM, DVDs or other optical storage, magnetic cassettes, magnetic tape, magnetic disk storage or other magnetic storage devices, or any other tangible, physical medium which may be used to store the desired information, and which may be accessed by the computing device 110. Any such non-transitory computer-readable media may be part of the computing device 110 or may be a separate database, databank, remote server, or cloud-based server.

In some implementations, the transceiver(s) 522 include any sort of transceivers known in the art. In some examples, the transceiver(s) 522 may include wireless modem(s) to facilitate wireless connectivity with a user device, the Internet, and/or an intranet via a cellular connection. Further, the transceiver(s) 522 may include a radio transceiver that performs the function of transmitting and receiving radio frequency communications via an antenna (e.g., Wi-Fi or Bluetooth®). In other examples, the transceiver(s) 522 may include wired communication components, such as a wired modem or Ethernet port, for communicating with the other user devices or the provider's Internet-based network. The transceiver(s) 522, may receive the input structure for the material. Also, the transceiver(s) 522 may send instructions to a remote device (e.g., an external server) that causes the remote device to display the visual simulation as a graphical user interface.

In some implementations, the output device(s) 524 include any sort of output devices known in the art, such as a display (e.g., a liquid crystal or thin-film transistor (TFT) display), a touchscreen display, speakers, a vibrating mechanism, or a tactile feedback mechanism. In some examples, the output devices may play various sounds based on, for example, whether the computing device 110 is connected to a network, the type of data being received, when the instructions are being transmitted, etc. Output device(s) 524 also include ports for one or more peripheral devices, such as headphones, peripheral speakers, or a peripheral display.

In various implementations, input device(s) 526 include any sort of input devices known in the art. For example, the input device(s) 526 may include a camera, a microphone, a keyboard/keypad, or a touch-sensitive display. A keyboard/keypad may be a standard push button alphanumeric, multi-key keyboard (such as a conventional QWERTY keyboard), virtual controls on a touchscreen, or one or more other types of keys or buttons, and may also include a joystick, wheel, and/or designated navigation buttons, or the like.

The specific configurations, machines, and the size and shape of various elements may be varied according to particular design specifications or constraints requiring the RNN 120, computing device 110, system 100, or method 200, 300, 400A, 400B constructed according to the principles of this disclosure. Such changes are intended to be embraced within the scope of this disclosure. The presently disclosed examples, therefore, are considered in all respects to be illustrative and not restrictive. The scope of the disclosure is indicated by the appended claims, rather than the foregoing description, and all changes that come within the meaning and range of equivalents thereof are intended to be embraced therein.

Figure 6:
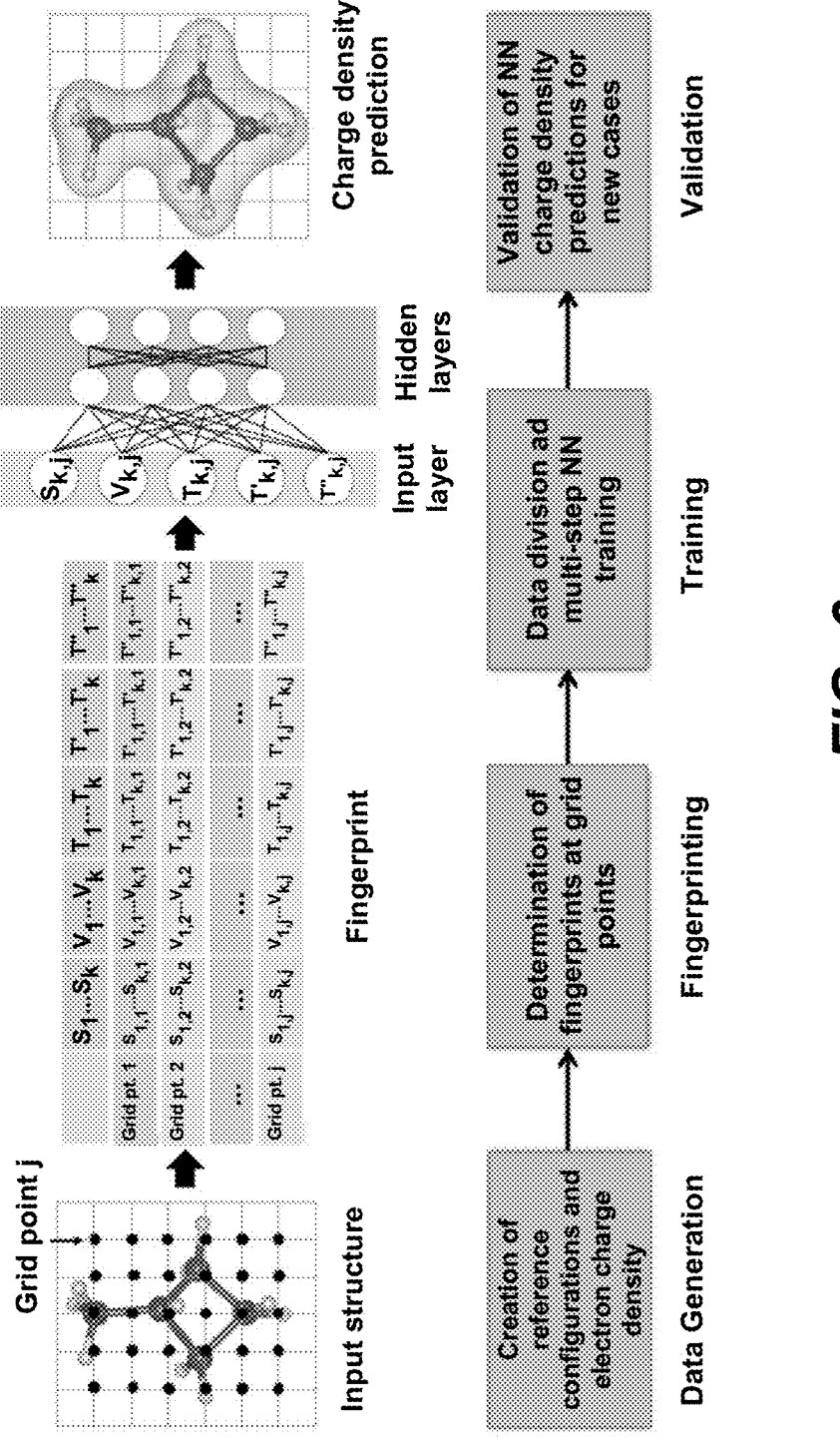
FIG. 6 is an image illustrating a method for simulating a material, in accordance with some examples of the present disclosure.

FIG. 6 is an image illustrating a method for simulating a material. The image may illustrate solving KS equations with a learning problem. The 3D arrangement of atoms at each grid point may be defined using a fingerprinting scheme. Then, the relationship between local arrangement of atoms and charge density at each grid point is learned using neural networks (e.g., RNN 120).

As shown, the method (e.g., method 300) may begin by receiving an input structure for a material. Next, a plurality of grid points for the input structure are identified. Of course, the scalar, vector, and tensorial component for each grid point is determined to help generate a respective fingerprint structure that is sent to the neural network (e.g., RNN 120). Based on the stored atomic configurations, the neural network sends an approximate total electronic density and a plurality of approximate energy levels for each grid point, which is used to generate a predict local density of states for each grid point and a total density of states. Once validated, this information can be used to improve the neural network, such that it can more accurately predict total electronic density and approximate energy levels in the future.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

In this description, numerous specific details have been set forth. It is to be understood, however, that implementations of the disclosed technology can be practiced without these specific details. In other instances, well-known methods, structures and techniques have not been shown in detail in order not to obscure an understanding of this description. References to "one embodiment," "an embodiment," "some embodiments," "example embodiment," "various embodiments," "one implementation," "an implementation," "example implementation," "various implementations," "some implementations," etc., indicate that the implementation(s) of the disclosed technology so described can include a particular feature, structure, or characteristic, but not every implementation necessarily includes the particular feature, structure, or characteristic. Further, repeated use of the phrase "in one implementation" does not necessarily refer to the same implementation, although it can.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and can include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for material fingerprinting with reduced computational requirements, the method comprising:

training, by a computing device, a recurrent neural network (RNN) to predict an approximate total electronic charge density and a plurality of approximate energy levels for a plurality of grid points based on a provided structure fingerprint by mapping the provided structure fingerprint to stored atomic configurations, wherein the RNN comprises three hidden layers with a plurality of neurons in each layer, and wherein the plurality of grid points comprise arrangements of millions of atoms of a first material;

receiving, by a transceiver of the computing device, an input structure for a second material, the input structure comprising arrangements of millions of atoms of the second material;

identifying, by a processor of the computing device and based on the input structure, a first reference grid point (g) for the second material;

determining, by the processor, a first scalar component for the second material, wherein the first scalar component comprises radial information of a plurality of atoms of the second material;

determining, by the processor, a first vector component for the second material based on the first reference grid point;

determining, by the processor, a first tensorial component for the second material based on the first reference grid point;

generating, by the processor, a first structure fingerprint (G) for the second material based on the first scalar component, the first vector component, and the first tensorial component;

wherein one or more of:

determining the first scalar component for the second material comprises applying an equation of:

$S\_kQ=c\_k\Sigma\_(i=1)^{(N\_\Omega)} \equiv [\![ exp((-[\![ r\_gi ]\!]^2)/[\![ 2\sigma ]\!]\_k ]\!]^2)f\_c ]\!](r_{gi})$, wherein $r_{gi}$ is an amount of distance between an atom (i) of a species $\Omega$ and the first reference grid point location is any cutoff function that decays to zero for the plurality of atoms at a distance greater than $R_c$ from the first reference grid point g, $c_k$ is a normalization constant given by $$\frac{1}{\sqrt{2\pi\sigma_k}},$$

$N_\Omega$ is a number of atoms of the species $\Omega$, and an overall dimensionality of the first scalar component is based on a number of Gaussians k and a type of the species $\Omega$;

determining the first vector component for the second material comprises applying an equation of:

$$V_{k\Omega}^{\alpha} = c_k \sum_{i=1}^{N_\Omega} \frac{r_{gi}^{\alpha}}{r_{gi}} \exp\left(\frac{-r_{gi}^2}{2\sigma_k^2}\right) f_c(r_{gi}),$$

wherein $\alpha$ represents each of the x, y, or z directions;

determining the first tensorial component for the second material comprises applying an equation of:

$$T_{k\Omega}^{\alpha\beta} = c_k \sum_{i=1}^{N_\Omega} \frac{r_{gi}^{\alpha} r_{gi}^{\beta}}{r_{gi}^2} \exp\left(\frac{-r_{gi}^2}{2\sigma_k^2}\right) f_c(r_{gi}),$$

wherein $\alpha$ represents each of the x, y, or z directions, and $\beta$ represents each of the x, y, or z directions; and generating the first structure fingerprint comprises applying a function to the first scalar component, the first vector component, and the first tensorial component;

generating, using the trained RNN, a first approximate total electronic charge density and a first plurality of approximate energy levels for the first reference grid point g based on the first structure fingerprint G;

determining, by the processor, a total electronic charge density for the first reference grid point g based on the approximate total electronic charge density generated by the trained RNN;

determining, by the processor, a local density of states for the first reference grid point g based on the first plurality of approximate energy levels generated by the trained RNN;

generating, by the processor, a first visual simulation of the second material based on the total electronic charge density and the local density of states;

displaying, by the computing device, the first visual simulation via a graphical user interface (GUI); and further training the RNN based on the determined total electronic charge density for the first reference grid point g and the determined local density of states for the first reference grid point g to improve the accuracy of the RNN.

2. The method of claim 1, wherein the first structure fingerprint for the second material is a numerical representation of the atomic arrangement around the first grid reference point of the second material.

3. The method of claim 2, further comprising rendering the first vector component rotationally invariant by: applying an equation of: $V_{k\Omega}=\sqrt{(V_{k\Omega}^{x})^2+(V_{k\Omega}^{y})^2+(V_{k\Omega}^{z})^2}$.

4. The method of claim 2, further comprising rendering the first tensorial component rotationally invariant by:

applying an equation of: $T'_{k\Omega}=T_{k\Omega}^{xx}T_{k\Omega}^{yy}+T_{k\Omega}^{yy}T_{k\Omega}^{zz}+T_{k\Omega}^{xx}T_{k\Omega}^{zz}-(T_{k\Omega}^{xy})^2-(T_{k\Omega}^{yz})^2-(T_{k\Omega}^{zx})^2$; and applying an equation of: $T''_{k\Omega}=\det T_{k\Omega}^{\alpha\beta}$.

5. The method of claim 2, further comprising rendering the first tensorial component rotationally invariant by: applying an equation of: $T'''_{k\Omega} = T_{k\Omega}^{xx} + T_{k\Omega}^{yy} + T_{k\Omega}^{zz}$.

6. The method of claim 2, wherein the RNN is located on a remote device.

7. The method of claim 1, further comprising sending, by the transceiver, instructions to a remote device that causes the remote device to display the first visual simulation as a second GUI.

8. The method of claim 1, further comprising:

identifying, by the processor, a second reference grid point ($g_2$) for the second material;

determining, by the processor, a second scalar component for the second material based on the second reference grid point;

determining, by the processor, a second vector component for the second material based on the second reference grid point;

determining, by the processor, a second tensorial component for the second material based on the second reference grid point;

generating, by the processor, a second structure fingerprint ($G_2$) for the second material based on the second scalar component, the second vector component, and the second tensorial component, wherein the second structure fingerprint comprises a numerical representation of the second structure fingerprint;

sending, by the processor, the second structure fingerprint to the RNN, wherein the RNN maps the second structure fingerprint to stored atomic configurations;

receiving, by the processor, a second plurality of approximate energy levels for the second reference grid point based on at least one corresponding stored atomic configuration, from the RNN;

generating, by the processor, a second predictive local density of states for the second reference grid point based on the second plurality of approximate energy levels; and calculating, by the processor, a total density of states (DOS) based on at least the local density of states for the first reference grid point and the second predictive local density of states.

9. A method for material simulation with reduced computational requirements, the method comprising:

training, by a computing device, a recurrent neural network (RNN) to predict an approximate total electronic charge density and a plurality of approximate energy levels for a plurality of grid points based on a provided structure fingerprint by mapping the provided structure fingerprint to stored atomic configurations, wherein the RNN comprises three hidden layers with a plurality of neurons in each layer, and wherein the plurality of grid points comprise arrangements of millions of atoms of a first material;

receiving, by a transceiver of the computing device, an input structure for a second material, the input structure comprising arrangements of millions of atoms of the second material;

identifying, by a processor of a computing device and based on the input structure, a first reference grid point (g) for the second material;

determining, by the processor, a first scalar component for the second material, wherein the first scalar component comprises radial information of a plurality of atoms of the second material;

determining, by the processor, a first vector component for the second material based on the first reference grid point;

determining, by the processor, a first tensorial component for the second material based on the first reference grid point;

generating, by the processor, a first structure fingerprint (G) for the second material based on the first scalar component, the first vector component, and the first tensorial component by applying one or more functions to the first scalar component, the first vector component, and the first tensorial component;

sending, by the processor, the first structure fingerprint to the RNN;

generating, using the trained RNN, a first approximate total electronic charge density and a first plurality of approximate energy levels for the first reference grid point g based on the first structure fingerprint G;

receiving, by the processor, the first approximate total electronic charge density for the first reference grid point based on at least one corresponding stored atomic configuration, from the RNN;

generating, by the processor, a predictive total electronic charge density for the first reference grid point based on the approximate total electronic charge density generated by the trained RNN;

receiving, by the processor, the first plurality of approximate energy levels for the first reference grid point based on at least one corresponding stored atomic configuration, from the RNN;

generating, by the processor, a first predictive local density of states for the first reference grid point based on the first plurality of approximate energy levels generated by the trained RNN;

generating, by the processor, a first visual simulation of the second material based on the first predictive local density of states and the predictive total electronic charge density;

displaying, by a graphical user interface of the computing device, the first visual simulation of the second material; and further training the RNN based on the generated predictive total electronic charge density for the first reference grid point g and the generated first predictive local density of states for the first reference grid point g to improve the accuracy of the RNN.

10. The method of claim 9, wherein determining the first scalar component for the second material comprises applying an equation of: $S\_kQ = c\_k\Sigma\_(i=1)^(N\_\Omega) \llbracket exp((-\llbracket r\_gi \rrbracket^2)/\llbracket \llbracket 2\sigma \rrbracket \_k \rrbracket^2)f\_c \rrbracket (r_{gi})$;

wherein $r_{gi}$ is an amount of distance between an atom (i) of a species $\Omega$ and the first reference grid point location is any cutoff function that decays to zero for the plurality of atoms at a distance greater than $R_c$ from the first reference grid point;

wherein $c_k$ is a normalization constant given by $$\frac{1}{\sqrt{2\pi\sigma_k}};$$

wherein $N_\Omega$ is a number of atoms of the species $\Omega$; and wherein an overall dimensionality of the scalar component is based on a number of Gaussians k and a type of the species $\Omega$.

11. The method of claim 9, wherein determining the first vector component for the second material comprises applying an equation of:

$$V_{k\Omega}^{\alpha} = c_k \sum_{i=1}^{N_\Omega} \frac{r_{gi}^{\alpha}}{r_{gi}} \exp\left(\frac{-r_{gi}^2}{2\sigma_k^2}\right) f_c(r_{gi});$$

and
wherein $\alpha$ represents each of the x, y, or z directions.

12. The method of claim 11, further comprising rendering the first vector component rotationally invariant by: applying an equation of: $V_{k\Omega} = \sqrt{(V_{k\Omega}^x)^2 + (V_{k\Omega}^y)^2 + (V_{k\Omega}^z)^2}$.

13. The method of claim 9, wherein determining the first tensorial component for the second material comprises applying an equation of:

$$T_{k\Omega}^{\alpha\beta} = c_k \sum_{i=1}^{N_\Omega} \frac{r_{gi}^{\alpha} r_{gi}^{\beta}}{r_{gi}^2} \exp\left(\frac{-r_{gi}^2}{2\sigma_k^2}\right) f_c(r_{gi});$$

wherein $\alpha$ represents each of the x, y, or z directions; and
wherein $\beta$ represents each of the x, y, or z directions.

14. The method of claim 13, further comprising rendering the first tensorial component rotationally invariant by:
applying an equation of: $T'_{k\Omega} = T_{k\Omega}^{xx}T_{k\Omega}^{yy} + T_{k\Omega}^{yy}T_{k\Omega}^{zz} + T_{k\Omega}^{xx}T_{k\Omega}^{zz} - (T_{k\Omega}^{xy})^2 - (T_{k\Omega}^{yz})^2 - (T_{k\Omega}^{zx})^2$; and
applying an equation of: $T''_{k\Omega} = \det T_{k\Omega}^{\alpha\beta}$.

15. The method of claim 13, further comprising rendering the first tensorial component rotationally invariant by: applying an equation of:

$$T'''_{k\Omega} = T_{k\Omega}^{xx} + T_{k\Omega}^{yy} + T_{k\Omega}^{zz}.$$

16. The method of claim 9, further comprising:
identifying, by the processor, a second reference grid point ($g_2$) for the second material;
determining, by the processor, a second scalar component for the second material based on the second reference grid point;
determining, by the processor, a second vector component for the second material based on the second reference grid point;
determining, by the processor, a second tensorial component for the second material based on the second reference grid point;
generating, by the processor, a second structure fingerprint ($G_2$) for the second material based on the second scalar component, the second vector component, and the second tensorial component, wherein the second structure fingerprint comprises a numerical representation of the second structure fingerprint;
sending, by the processor, the second structure fingerprint to the RNN, wherein the RNN maps the second structure fingerprint to stored atomic configurations;
receiving, by the processor, a second plurality of approximate energy levels for the second reference grid point based on at least one corresponding stored atomic configuration, from the RNN;
generating, by the processor, a second predictive local density of states for the second reference grid point based on the second plurality of approximate energy levels; and calculating, by the processor, a total density of states (DOS) based on at least the first predictive local density of states and the second predictive local density of states.

17. A system for material simulation with reduced computational requirements, the system comprising:
a computing device comprising:
a processor;
a transceiver; and
a graphical user interface;
a recurrent neural network (RNN); and
memory, in communication with the processor, the transceiver, the RNN, and the graphical user interface, storing instructions, that when executed, cause the system to:
train, by the computing device, the RNN to predict an approximate total electronic charge density and a plurality of approximate energy levels for a plurality of grid points based on a provided structure fingerprint by mapping the provided structure fingerprint to stored atomic configurations, wherein the RNN comprises three hidden layers with a plurality of neurons in each layer, and wherein the plurality of grid points comprise arrangements of millions of atoms of a first material;
receive, by the transceiver, an input structure for a second material, the input structure comprising arrangements of millions of atoms of the second material;
identify, by the processor, a first reference grid point (g) for the second material;
determine, by the processor, a first scalar component for the second material, wherein the first scalar component comprises radial information of a plurality of atoms of the second material;
determine, by the processor, a first vector component for the second material based on the first reference grid point;
determine, by the processor, a first tensorial component for the second material based on the first reference grid point;
generate, by the processor, a first structure fingerprint (G) for the second material based on the first scalar component, the first vector component, and the first tensorial component;
wherein one or more of:
determining the first scalar component for the second material comprises applying an equation of:
$S\_kQ = c\_k\Sigma\_(i=1)^\wedge(N\_\Omega) ⁂ ⟦ \exp((-⟦ r\_gi⟧ ^2)/⟦ ⟦ 2\sigma⟧ \_k⟧ ^2)f\_c ⟧ (r_{gi})$, wherein $r_{gi}$ is an amount of distance between an atom (i) of a species $\Omega$ and the first reference grid point location is any cutoff function that decays to zero for the plurality of atoms at a distance greater than $R_c$ from the first reference grid point g, $c_k$ is a normalization constant given by $$\frac{1}{\sqrt{2\pi}\sigma_k},$$

$N_\Omega$ is a number or atoms or the species $\Omega$, and an overall dimensionality of the first scalar component is based on a number of Gaussians k and a type of the species $\Omega$;

determining the first vector component for the second material comprises applying an equation of:

$$V_{k\Omega}^{\alpha} = c_k \sum_{i=1}^{N_\Omega} \frac{r_{gi}^{\alpha}}{r_{gi}} \exp\left(\frac{-r_{gi}^2}{2\sigma_k^2}\right) f_c(r_{gi}),$$

wherein $\alpha$ represents each of the x, y, or z directions; determining the first tensorial component for the second material comprises applying an equation of:

$$T_{k\Omega}^{\alpha\beta} = c_k \sum_{i=1}^{N_\Omega} \frac{r_{gi}^{\alpha} r_{gi}^{\beta}}{r_{gi}^2} \exp\left(\frac{-r_{gi}^2}{2\sigma_k^2}\right) f_c(r_{gi}),$$

wherein $\alpha$ represents each of the x, y, or z directions, and $\beta$ represents each of the x, y, or z directions; and generating the first structure fingerprint comprises applying a function to the first scalar component, the first vector component, and the first tensorial component;

generate, using the trained RNN, a first approximate total electronic charge density and a first plurality of approximate energy levels for the first reference grid point g based on the first structure fingerprint G;

determine, by the processor, a total electronic charge density for the first reference grid point g based on the approximate total electronic charge density generated by the trained RNN;

determine, by the processor, a first predictive local density of states for the first reference grid point g based on the first plurality of approximate energy levels generated by the trained RNN;

generate, by the processor, a first visual simulation of the second material based on the total electronic charge density and the first predictive local density of states;

display, by the graphical user interface, the first visual simulation; and further train the RNN based on the determined total electronic charge density for the first reference grid point g and the determined first predictive local density of states for the first reference grid point g to improve the accuracy of the RNN.

18. The system of claim 17, wherein the system is further configured to:

identify, by the processor, a second reference grid point ($g_2$) for the second material;

determine, by the processor, a second scalar component for the second material based on the second reference grid point;

determine, by the processor, a second vector component for the second material based on the second reference grid point;

determine, by the processor, a second tensorial component for the second material based on the second reference grid point;

generate, by the processor, a second structure fingerprint ($G_2$) for the second material based on the second scalar component, the second vector component, and the second tensorial component, wherein the second structure fingerprint comprises a numerical representation of the second structure fingerprint;

map, by the RNN, the second structure fingerprint to stored atomic configurations;

determine, by the RNN, a second plurality of approximate energy levels for the second reference grid point based on at least one corresponding stored atomic configuration;

determine, by the processor, a second predictive local density of states for the second reference grid point based on the second plurality of approximate energy levels; and calculate, by the processor, a total density of states (DOS) based on at least the first predictive local density of states for the first reference grid point and the second predictive local density of states.

* * * * *